United States Patent [19]

Gutcho et al.

[11] 4,423,154

[45] Dec. 27, 1983

[54] SIMULTANEOUS RADIOASSAY OF FOLATE AND VITAMIN B12

[75] Inventors: Sidney Gutcho, Monsey; Lillian Mansbach, New City, both of N.Y.

[73] Assignee: Becton Dickinson and Company, Paramus, N.J.

[21] Appl. No.: 233,855

[22] Filed: Feb. 12, 1981

Related U.S. Application Data

[60] Division of Ser. No. 919,387, Jun. 26, 1978, Pat. No. 4,279,859, which is a continuation-in-part of Ser. No. 817,563, Jul. 21, 1977, Pat. No. 4,146,602, which is a continuation-in-part of Ser. No. 762,992, Jan. 27, 1977, abandoned.

[51] Int. Cl.$^3$ .................... G01N 33/56; G01N 33/60; B07D 71/00
[52] U.S. Cl. .................................. 436/505; 436/545; 436/804
[58] Field of Search ................. 424/1, 112; 23/230 B; 422/61; 436/505, 545

[56] References Cited

U.S. PATENT DOCUMENTS

| | | | |
|---|---|---|---|
| 3,937,799 | 2/1976 | Lewin et al. | 23/230 B |
| 3,952,091 | 4/1976 | Grunberg et al. | 424/1.5 |
| 3,972,991 | 8/1976 | Caston et al. | 424/12 |
| 3,981,863 | 9/1976 | Niswender et al. | 424/12 |
| 3,988,431 | 10/1976 | Givas et al. | 23/230 B |
| 4,146,602 | 3/1979 | Gutcho et al. | 424/1 |
| 4,279,859 | 7/1981 | Gutcho et al. | 422/61 |

*Primary Examiner*—Christine M. Nucker
*Attorney, Agent, or Firm*—Elliot M. Olstein; Louis E. Marn

[57] ABSTRACT

A serum sample is heated at an alkaline pH to release folate and vitamin $B_{12}$ from endogenous binders. A simultaneous radioassay for folate and vitamin $B_{12}$ is effected by contacting the sample with binder for folate, binder for vitamin $B_{12}$, folate labeled with one radioactive isotope and vitamin $B_{12}$ labeled with another radioactive isotope, followed by separation of bound and free portions, and determination of the radioactivity of at least one of the portions. The amounts of folate and vitamin $B_{12}$ present in the sample may be determined from standard curves.

17 Claims, No Drawings

SIMULTANEOUS RADIOASSAY OF FOLATE AND VITAMIN B12

This is a division, of application Ser. No. 919,387, filed June 26, 1978 U.S. Pat. No. 4,279,859 which is a continuation in part of U.S. application No. 817,563 filed July 21, 1977 now U.S. Pat. No. 4,146,602, which is a continuation in part of U.S. application Ser. No. 762,992 filed on Jan. 27, 1977 abandoned.

This invention relates to radioassay, and more particularly, to a radioassay for folate and vitamin $B_{12}$.

Currently, endogenous folate is measured by a competitive protein-binding technique. In brief, competitive protein-binding(CPB) for the assay of folate involves the ability of unlabeled folate in serum or other media to compete with labeled folic acid for a specific folate binder, present in usable concentrations in such sources as cow's milk, hog kidney, etc., and thereby inhibit the binding of labeled folic acid. As a result of the competitive inhibition, the ratio of bound labeled folic acid to free labeled folic acid diminishes as the concentration of unlabeled folate is increased. Accordingly, the concentration of folate in an unknown sample; e.g., a patient's serum, is obtained by comparing the inhibition observed with that produced by known amounts of folate, as presented in a standard curve.

Endogenous vitamin $B_{12}$ is also determined by a similar competitive protein-binding technique, with the vitamin $B_{12}$ binder generally being hog intrinsic factor.

The present invention is directed to an improved radioassay wherein the folate and vitamin $B_{12}$ present in a sample may be determined simultaneously.

In accordance with the present invention, a sample containing folate and vitamin $B_{12}$ is contacted with a binder for the folate, a binder for the vitamin $B_{12}$, a folate tracer labeled with a first radioactive isotope and a vitamin $B_{12}$ tracer labeled with a second radioactive isotope different from the first radioactive isotope, resulting in competitive binding between the labeled and unlabeled folate and the labeled and unlabeled vitamin $B_{12}$ for their respective binder sites. The bound portions of labeled and unlabeled folate and bound portions of labeled and unlabeled vitamin $B_{12}$ are simultaneously separated from the unbound portions of labeled and unlabeled folate and unbound portions of labeled and unlabeled vitamin $B_{12}$, followed by counting the radioactivity of at least one of the bound or unbound portions, with the amounts of folate and vitamin $B_{12}$ then being determined from standard curves.

In accordance with the present invention, folate and vitamin $B_{12}$ are released from their endogenous binders by heating a sample, containing folate and vitamin $B_{12}$; e.g., a serum or plasma sample, with the endogenous binders being destroyed by such heating. The heating can be effected at a wide variety of pH values, with the pH generally being 5 or greater. The pH is most generally at least 7.0 (neutral or alkaline pH), with the pH preferably being at least 9.0 and perferably no greater than 9.6. The most preferred pH is from 9.2 to 9.4 (generally 9.3) in that this permits the release to be effected at the same pH as the subsequent assay in which folic acid is employed as a standard, instead of the reduced methyl derivaative of frolic acid. The heating to release vitamin $B_{12}$ and folate from their binders is generally effected at a temperature of from about 95° C. to about 110° C., and preferably of from about 98° C. to about 105° C.

The release of folic acid and vitamin $B_{12}$ from their endogeneous binders is also effected in the presence of a suitable reducing agent in order to preserve the endogenous folate present in the serum in reduced form. The reducing agent which is included during the heating step is a reducing agent which maintains the reduced folate without adversely affecting the vitamin $B_{12}$ and which is stable under the assay conditions. As representative examples of suitable reducing agents there may be mentioned: ascorbate, Cleland's reagent (dithiothreitol;) dithioerythritol; monothioglycol; thiodiglycol; thioglycollic acid; crysteine; homocysteine; gluthathione; mercaptoethanol; sulfhydryl reducing agents; inorganic reducing agents, such as sodium sulfite; sodium dithionite; sodium sulfide, sodium metabisulfite, with the organic reducing agents being preferred.

After release of folic acid and vitamin $B_{12}$ from their endogenous binders and destruction of such endogenous binders, the sample is contacted with a dual tracer; i.e., a tracer for folate and a tracer for vitamin $B_{12}$, and a dual binder; i.e., a binder for folate and a binder for vitamin $B_{12}$. The receptors, both naturally occurring and antibodies, for folate are well known in the art, and any one of such receptors may be employed in the assay of the present invention. As representative examples of such receptors, there may be mentioned: receptors or binders extracted from various animal organs particularly kidneys and pancreas; $\beta$-lactoglobulin preparations; cow's milk, dolphin serum and the like, with milk binder being preferred. Similarly, binders or receptors for vitamin $B_{12}$ are known in the art, e.g., saliva, chicken serum, intrinsic factor, with the preferred binder being intrinsic factor.

The folic tracer is either folic acid (pteroylmonoglutamic acid) (PGA) [or the reduced 5-methyl derivative of folic acid, 5-methyltetrahydrofolic acid (MTFA)] or appropriate analogs thereof, labeled with a radioactive isotope, which is preferably a radioactive isotope of iodine. The term folate tracer generically refers to radiolabeled folic acid, the radiolabeled reduced 5-methyl derivative and the radiolabeled analogs thereof. The 5-methyl derivative is generally not employed as a tracer as a result of the instability thereof. The radiolabeled folate employed as a tracer is preferably radiolabeled folic acid, and the term radiolabeled folic acid includes the radiolabeled analogs thereof: i.e., folic acid substituted with a radiolabeled radical. The preferred radioactive isotope is a radioactive isotope of iodine, and most preferably $I^{125}$ with the tracer being a folic acid including a substituent which includes a radioiodinated phenol or imidazole group such as histidine, histamine, tyrosine or tyramine, which is substituted with a radioactive isotope of iodine. A particularly preferred tracer is one in which the $\alpha$-carboxyl group of the glutamyl moiety is substituted with radioiodinated tyrosyl or histidyl, as disclosed in U.S. Application Ser. No. 727,408, filed Sept. 29, 1976 hereby incorporated by reference; however, it is to be understood that the tracer can also be one in which the $\gamma$-carboxyl group is so substituted, as disclosed in U.S. Pat. No. 3,989,812.

The vitamin $B_{12}$ tracer is preferably a radiolabeled vitamin $B_{12}$, with the vitamin $B_1$ preferably being labeled with $^{57}Co$.

In accordance with the preferred procedure, the assay is effected at an alkaline pH; i.e., the assay and release of folate and vitamin $B_{12}$ from binders are both effected at alkaline pH, with the release being effected at temperatures known in the art; i.e., generally in the order of from about 98° C. to 105° C. It is to be understood that the release and subsequent assay could be effected at different pH values; however, identical pH values are preferably employed in that this eliminates the necessity for a pH adjustment.

In accordance with the most preferred procedure for effecting the assay, folate and vitamin $B_{12}$ are released from their endogenous binders at an alkaline pH in the order of from about 9.2 to 9.4 followed by effecting the assay at a pH of from about 9.2 to about 9.4 with the folate tracer being in the form of a radioiodinated folic acid, with the radio-iodinated folic acid preferably being a radioiodinated analog of folic acid; e.g., radioiodo-substituted histidyl, tyrosyl or tyramyl, preferably tyrosyl. The tracer for vitamin $B_{12}$ is $^{57}Co$ labeled vitamin $B_{12}$. The use of radiolabeled folic acid and assay of endogenous folates at such a pH permits the use of folic acid as a standard, instead of MTFA, as described in U.S. Pat. No. 3,988,431.

It is to be understood that in accordance with the preferred procedure wherein folic acid is employed as a standard, even though the assay should be effected at pH 9.2-9.2, the release from binder can be effected at another pH value. Similarly, if the standard for the assay is MTFA, the assay and/or release can be effected at pH value other than 9.2-9.4.

The bound and unbound portions are separated by procedures known in the art, with such portions generally being separated by the use of a particulate adsorbent. The preferred adsorbent is dextran-coated charcoal; however, it is to be understood that any one of a wide variety of other adsorbents, such as ion exchange resins, inorganic adsorbents, etc., may be employed for separating the bound and free portions. In addition, the assay may be effected by a so-called solid phase assay technique, wherein the receptors for folate and vitamin $B_{12}$ are previously coated on or bound to a solid support, such as a test tube, or insoluble polymer, whereby the bound and free portions may be readily separated from each other. The techniques for effecting separation of bound and free portions, whether by the addition of a particulate adsorbent, or by the use of a receptor bound to a solid phase, forms no part of the present invention.

After separation of the bound and free portions, the radioactivity of either the bound or free portion or both portions is determined, and the determined radioactivity is compared with a standard curve, by procedures known in the art. As should be apparent, since different radioactive isotopes are employed for labeling the folate tracer and vitamin $B_{12}$ tracer, the respective tracers may be counted in different channels of a counter or if the counter has one channel, it can be calibrated so that different counter settings will count one isotope at a time.

The invention will be further described with respect to the following example; however, the scope of the invention is not to be limited thereby.

EXAMPLE

The following reagents are used in the dual assay:
1. Dual Tracer
   1.5$\mu$ Ci $\alpha$—(pteroylglutamyl)$^{125}I$-L-tyrosine (prepared s described in U.S. Application Ser. No. 727,408) and 0.75$\mu$ Ci vitamin $B_{12}[^{57}Co]$, human serum albumin, sodium borate, dextran and prevatives
2. Dual Binder
   Folate binder from bovine milk and hog intrinsic factor, both formulated for a trace binding (Bo) of 55±15%, human serum albumin, dextran and preservatives.
3. Dual Standards containing human serum albumin, sodium borate, sodium chloride and preservatives.

| 3A | Dual Standard A | Zero level |
|----|-----------------|------------|
| 3B | Dual Standard B | 1.0 ng/ml Folic acid; 100 pg/ml $B_{12}$ |
| 3C | Dual Standard C | 2.0 ng/ml Folic acid; 200 pg/ml $B_{12}$ |
| 3D | Dual Standard D | 4.0 ng/ml Folic acid; 400 pg/ml $B_{12}$ |
| 3E | Dual Standard E | 10 ng/ml Folic acid; 1000 pg/ml $B_{12}$ |
| 3F | Dual Standard F | 20 ng/ml Folic acid; 2000 pg/ml $B_{12}$ |

4. Buffer pH 9.3, 0.05 M sodium borate with 6.25$\mu$ g potassium cyanide/ml.
5. Cleland's Reagent (dithiothreitol) solution, 5%.
5A. Assay Buffer
    A mixture of 1 ml of Reagent 5 to 50 ml of Reagent 4.
6. Dextran-coated charcoal suspension, 4.4±0.1 g dextrancharcoal dry mix (1:10), suspending agent and sodium chloride in 100 ml sterile distilled water.

| PROTOCOL | |
|---|---|
| Preparation of a Standard Curve | Clinical Determinations |
| 1. Number 18 polypropylene tubes sequentially from 1-16. | 1. Starting with 17, consecutively number two polypropylene tubes for each clinical sample. |
| 2. Add assay Buffer (Reagent 5A) as follows:<br>Tubes  Buffer<br>1,2      1600 $\mu$l<br>3-16    1000 $\mu$l | 2. Add 1000 $\mu$l Assay Buffer (Reagent 5A) to each tube. |
| 3. Add Dual Standards (Reagents 3A-3F) as follows: | 3. Add 100 $\mu$l patient sample to each of two tubes. Mix gently. |

| Tube No. | Standard | Folic Acid as ng/ml | Vitamin $B_{12}$ as pg/ml |
|----------|----------|---------------------|---------------------------|
| 3-6 | 100 $\mu$lA | 0 | 0 |
| 7,8 | 100 $\mu$lB | 1.0 | 100 |
| 9,10 | 100 $\mu$lC | 2.0 | 200 |
| 11,12 | 100 $\mu$lD | 4.0 | 400 |
| 13,14 | 100 $\mu$lE | 10 | 1000 |
| 15,16 | 100 $\mu$lF | 20 | 2000 |

Mix gently.
4. Cover all tubes loosely with plastic caps (except 1 and 2).
5. Heat all tubes (except 1 and 2) in a glycerin or water bath at 100° C. for 45 minutes.
6. Remove all tubes from 100° C. bath. Cool to 20°-25° C. in a running water bath. Do not continue assay until the tubes are within this range. Uncap all tubes.

| | |
|---|---|
| 7. Add 100 $\mu$l Dual Tracer (Reagent 1) to all tubes. Mix gently by hand. Set tubes 1 and 2 aside at room temperature until Step 15. | 7. Add 100 $\mu$l Dual Tracer (Reagent 1) to each tube. Mix gently by hand. |
| 8. Add 100 $\mu$l Dual Binder (Reagent 2) to tubes 5-16. Mix gently by hand. | 8. Add 100 $\mu$l Dual Binder (Reagent 2) to each tube. Mix gently by hand. |

From this point, all tubes are treated as follows:
9. Incubate at room temperature for 45 minutes from the time of the last addition of the binder. Cover the rack of tubes with aluminum foil to exclude light or keep in the dark.

10. Add 0.4 ml dextran-coated charcoal to tubes 3–16 and to all patient sample tubes (17, 18, etc.). Do not add to tubes 1 and 2. This reagent is "squirted" into each tube to obtain a uniform suspension in the reaction mixture.
11. Keep at room temperature for 10 minutes from the time of last addition in Step 10.
12. Centrifuge at a minimum of 1240×g for 15 minutes, preferably in the cold. Shorter times may be sufficient in equipment of higher centrifugal force.
13. Consecutively number a set of clean tubes, beginning with 3.
14. Gently decant each clear supernatant into the similarly numbered tube prepared in Step 13. Maximal transfer is obtained by hitting the rims together. Avoid decanting over any charcoal to the counting tube. Discard the charcoal residues.
15. Count the radioactivity in the supernatants and tubes 1 and 2 in sequence for one or more minutes with a scintillation (gamma) counter.

If the counter has two or more channels it should be calibrated to count [$^{125}$I] in one channel and [$^{57}$Co] in another. If the counter has one channel it should be calibrated so that different counter settings will count one isotope at a time. In the case of the latter, it will be necessary to count the tubes twice, once setting the counter for [$^{125}$I] and obtaining the folate curve counts and sample counts, then setting the counter for [$^{57}$Co] to obtain the Vitamin B$_{12}$ curve counts and sample counts. If in counting one isotope there is spillover from the other isotope, counter adjustments must be made. Decreasing channel widths can minimize or eliminate such spillover.

The folate curve and values are calculated from the counts obtained by counting [$^{125}$I]; the vitamin B$_{12}$ curve and values are obtained by counting [$^{57}$Co].

As the radioactive tracer decays with age, increased counting times may be required. (This will be unnecessary with efficient equipment). The volume of tracer used must be that specified in this protocol; tracer volume should not be increased to compensate for decay. Binding of each vitamin to its respective remains essentially unchanged with time using the volume of tracer specified. Reproducible results will be obtained by following the protocol which has been described.

The Standard Curve covers the range of 1.0 to 20 ng/ml folate and 100 to 2000 pg/ml of Vitamin B$_{12}$. A "Blank" (tubes 3 and 4) is used to correct for background counts and radioactive tracer which is not adsorbed onto the charcoal.

The present invention is particularly advantageous in that it is possible to effect a simultaneous assay for folate and vitamin B$_{12}$. Moreover, in accordance with the particularly preferred embodiments. Applicant unexpectedly found that vitamin B$_{12}$ and folate can both be effectively released from their endogenous binders and effectively assayed at an alkaline pH.

Numerous modifications and variations of the present invention are possible in light of the above teachings, and therefore, within the scope of the appended claims, the invention may be practiced otherwise than as particularly described.

We claim:

1. A reagent for use in effecting a simultaneous assay for folate and vitamin B$_{12}$ comprising:
   a dual tracer comprising an admixture of a folate tracer labeled with a first radioactive isotope and a vitamin B$_{12}$ tracer labeled with a second radioactive isotope different from said first isotope.
2. A reagent as set forth in claim 1 wherein said first isotope is radioiodine.
3. A reagent as set forth in claim 1 wherein said second isotope is radiocobalt.
4. A reagent as set forth in claim 2 wherein said second isotope tracer is radiocobalt.
5. A reagent as set forth in claim 1 wherein said first isotope is $^{125}$I.
6. A reagent as set forth in claim 1 wherein said second isotope is $^{57}$Co.
7. A reagent as set forth in claim 5 wherein said second isotope is $^{57}$Co.
8. A reagent as set forth in claim 1 wherein said folate tracer is folic acid in which a carboxyl group of the glutamyl moiety is substituted with a member selected from the group consisting of radioiodinated histidyl, radioiodinated tyramyl, radioiodinated histamyl and radioiodinated tyrosyl.
9. A reagent as set forth in claim 8 wherein said member is $^{125}$I-L-tyrosyl.
10. A reagent for use in effecting a simultaneous assay for folate and vitamin B$_{12}$ comprising:
    a dual binder comprising an admixture of a binder for folate and a binder for vitamin B$_{12}$.
11. A reagent as set forth in claim 10 wherein said folate binder is a bovine milk binder.
12. A reagent as set forth in claim 10 wherein said vitamin B$_{12}$ binder is hog intrinsic factor.
13. A reagent as set forth in claim 11 wherein said vitamin B$_{12}$ binder is hog intrinsic factor.
14. A reagent for use in effecting a simultaneous assay for folate and vitamin B$_{12}$ comprising:
    a dual standard comprising an admixture of a standard for folate and a standard for vitamine B$_{12}$.
15. A reagent as set forth in claim 14 wherein said folate standard is folic acid.
16. A reagent kit for use in effecting a simultaneous assay for folate and vitamin B$_{12}$ comprising:
    a dual tracer comprising an admixture of a folate tracer labeled with a first radioactive isotope and a vitamin B$_{12}$ tracer labeled with a second radioactive isotope different from said first isotope; and
    a plurality of dual standards, each comprising a premeasured standard for folate and a premeasured standard for vitamin B$_{12}$.
17. A reagent kit for use in effecting a simultaneous assay for folate and vitamin B$_{12}$ comprising:
    a plurality of dual standards, each comprising a premeasured standard for folate and a premeasured standard for vitamin B$_{12}$; and
    a dual binder comprising an admixture of a binder for folate and a binder for vitamin B$_{12}$.

* * * * *